(12) United States Patent
Bombardelli et al.

(10) Patent No.: US 6,419,950 B2
(45) Date of Patent: Jul. 16, 2002

(54) EXTRACTS OF ZANTHOXYLUM BUNGEANUM, AND PHARMACEUTICAL AND COSMETIC FORMULATIONS CONTAINING SAME

(75) Inventors: Ezio Bombardelli; Bruno Gabetta, both of Milan (IT)

(73) Assignee: Indena SpA, Milan (IT)

( * ) Notice: Subject to any disclaimer, the term of this patent is extended or adjusted under 35 U.S.C. 154(b) by 0 days.

(21) Appl. No.: 09/749,448

(22) Filed: Dec. 28, 2000

Related U.S. Application Data

(63) Continuation of application No. PCT/EP99/02358, filed on Jul. 4, 1999.

(30) Foreign Application Priority Data

Jul. 7, 1998 (IT) .......................................... MI98A1542

(51) Int. Cl.⁷ ............................. A61K 9/48; A01N 65/00
(52) U.S. Cl. ...................... 424/452; 424/725; 424/43; 424/59; 424/73; 424/455; 424/465
(58) Field of Search ......................... 424/725, 73, 452, 424/455, 465, 43, 59

(56) References Cited

FOREIGN PATENT DOCUMENTS

JP      01 294657 A     11/1989

OTHER PUBLICATIONS

Computer DWPI Abstract 1990–012982 JP01294657A Nov. 1989.*

Computer IFSCC Abstract 23627 Cristoni et l "In–Cosmetics" Apr. 20–22, 1999 P342–353.*

Kenji Mizutani et al. "Amides from Huajiao; Pericarps of Zanthoxylum Bungeanum Maxim." Chemical and Pharmaceutical Bulletin, vol. 36, No. 7, 1988, pp. 2362–2365.

Xin–Li Huang et al. "Effects of Extracts of Zanthoxylum Fruit and their Constituents on Spontaneous Beating Rate of Myocardial Cell Sheets in Culture." Phytotherapy Research, vol. 7, No. 1, 1993, pp. 41–48.

* cited by examiner

*Primary Examiner*—Herbert J. Lilling
(74) *Attorney, Agent, or Firm*—Pennie & Edmonds LLP

(57) ABSTRACT

The extract of the pericarp of *Zanthoxylum bungeanum,* prepared by extraction with carbon dioxide in supercritical conditions, has remarkable analgesic activity without exerting the local anesthetic activity characteristic of the extracts obtained by solvent means. The product of the present invention is prepared by extracting the pericarp of *Zanthoxylurn bungeanum,* finely ground or transformed into pellets, with carbon dioxide under pressure conditions ranging from 150 to 300 bars at temperatures ranging from 35 to 55° C.

6 Claims, 1 Drawing Sheet

EXTRACTS OF ZANTHOXYLUM BUNGEANUM, AND PHARMACEUTICAL AND COSMETIC FORMULATIONS CONTAINING SAME

CROSS-REFERENCE TO RELATED APPLICATIONS

This application is a continuation of the U.S. National Stage designation of co-pending International Patent Application PCT/EP99/02358, filed Jul. 4, 1999 the content of which is expressly incorporated herein by reference thereto.

FIELD OF THE INVENTION

The present invention relates to a novel extract obtained by extraction of the pericarp of Zanthoxylum bungeanum with carbon dioxide and to the pharmaceutical and cosmetic formulations containing it. This extract has anti-inflammatory and analgesic activities and can be used for the treatment of itching.

BACKGROUND OF THE INVENTION

Pericarp of Zanthoxylum bungeanum is commonly used in China in spices for seasoning food. Moreover, in Chinese and Indian folk medicine, this part of the plant is used as local anesthetic and for the treatment of dysentery. The essential oil, which contains a series of monoterpenes such as 1,8-cimol, linalool, 4-terpinol, caryophyllene, limonene and the like, is also reported as a strong repellent against insects.

Recently, EP 568001 disclosed the antiviral activity of the skin of this fruit. In U.S. Pat. No. 5,137,912, chelcrythrine extracted from the root bark of Zanthoxylum simulans (synonym of bungeanum) was disclosed to be active in the prevention of thrombosis. According to JP 01294657, the extraction of the pericarp with organic solvents provides an extract containing isobutylamides that exerts a local anesthetic effect 30 seconds after application on the tongue and lasting up to 20–80 minutes.

Despite this, there remains a need for additional anti-inflammatory and analgesic formulations, and the present invention satisfies this need.

SUMMARY OF THE INVENTION

It has now surprisingly been found that the extract of the pericarp of Zanthoxylum bungeanum, prepared by extraction with carbon dioxide under supercritical conditions, has remarkable analgesic activity without exerting the local anesthetic activity characteristic of the extracts obtained by solvent means. The product of the present invention is prepared by extracting the pericarp of Zanthoxylurn bungeanum, finely ground or transformed into pellets, with carbon dioxide under pressure conditions ranging from 150 to 300 bars, preferably under 180–230 bars, at temperatures ranging from 35 to 55° C., preferably at 35–40° C.

The resulting extract can either be used as it is, after removing the extraction water, or it can further be purified by partitioning it with immiscible solvents such as aliphatic alcohols and aliphatic hydrocarbons, preferably n-hexane or petroleum ether.

The resulting extracts proved to exert a marked analgesic activity when applied percutaneously to humans; therefore they are valuable for use both in the pharmaceutical and cosmetic fields.

In the pharmaceutical field, these extracts are useful for alleviating pain resulting from diabetic microangiopathy, hemorrhoids, burns, or due to any other local causes. A further application of the extracts of the invention is in the treatment of itching.

In the cosmetic field, the extracts according to the invention are useful in depilatory creams, after-sun formulations, shaving lotions and creams, and in all types of skin treatments requiring local analgesic or anti-itching action.

DETAILED DESCRIPTION OF THE INVENTION

Figure 1:
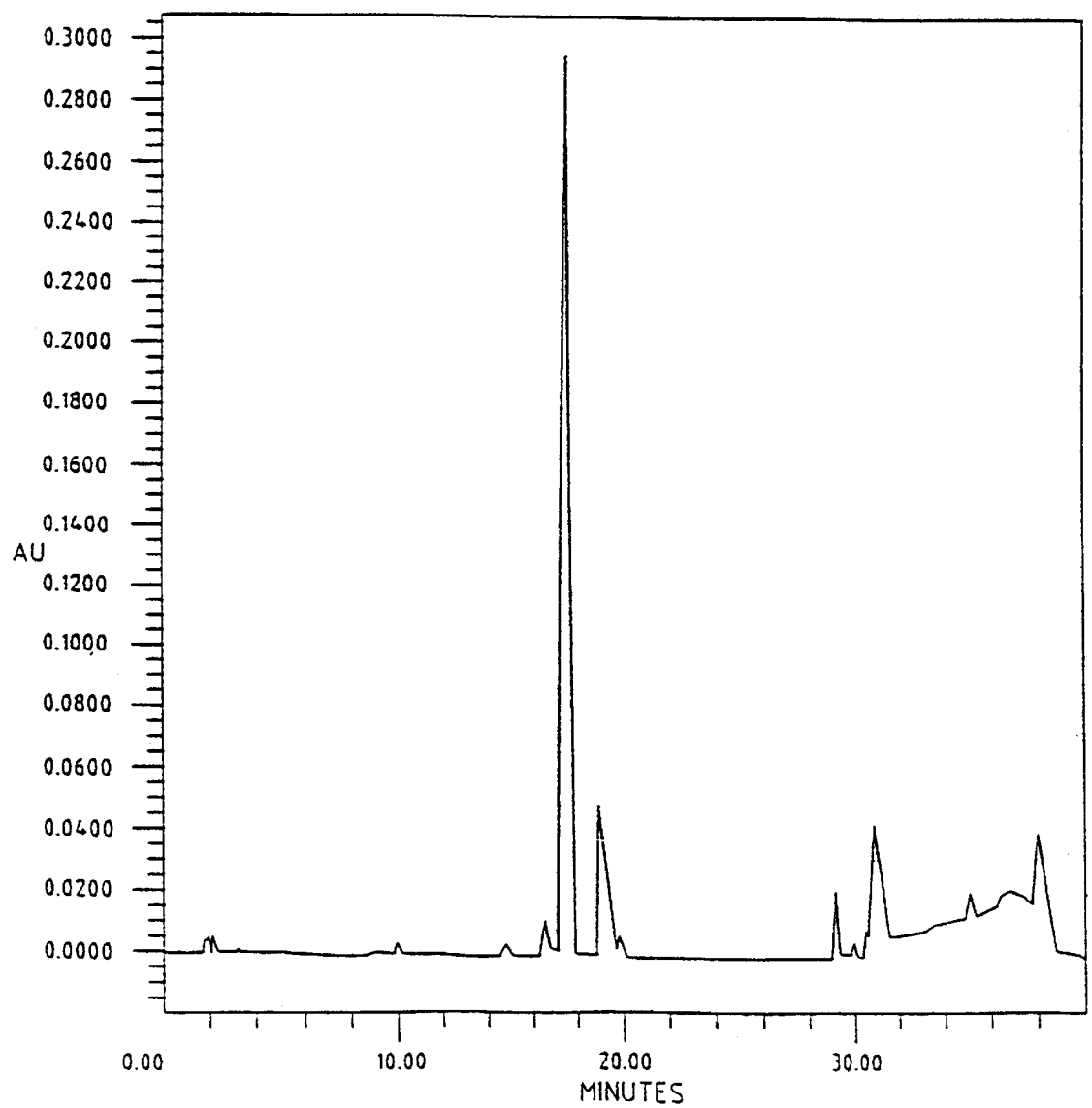
FIG. 1 is a chromatogram of an extract according to the invention.

The anti-itching activity of the extracts of the invention was evaluated through electrophysiological measurements using the experimental model of the rat ischiatic nerve-musculus extensor digitorum longus (EDL) preparation in vitro.

Adult Sprague-Dawley rats killed by an intracardial Penthotal overdose were used. The EDL muscle with a long tract of ischiatic nerve was dissected and placed in a container for electrophysiology with a Ringer solution which was substituted every 10 minutes. The tested extracts, preferably added with a surfactant, were dispersed in different concentrations, thereby coming into contact with nerve fibers, neuromuscular junctions and muscle. For the electrophysiological tests, an intracellular microelectrode filled with 3M KCl was placed in muscle cells for recording the electrical phenomena (miniature endplate potentials, endplate potentials, membrane potentials of the muscle cell) both spontaneous and induced by stimulation of the nerve. For this purpose, the nerve was linked to a stimulator and optionally stimulated once a second. The electric events in the muscle cells were detected by a microelectrode linked to a signal amplifier and made visible through a digital oscilloscope.

The extracts of the invention, when tested at concentrations ranging from 0.0005 to 0.002%, exerted a strong transitory activating action on the neuromuscular synaptic transmission, evidenced by the increase in the frequency of the miniature endplate potentials and by the appearance of spontaneous endplate potentials. Conversely, the extracts obtained with solvents; having local anesthetic activity, reduced and inhibited the transmission of the nervous impulse.

The analgesic activity of the tested extracts was evaluated in 10 healthy volunteers through an evaluation study of the skin thermal sensitivity.

A progressively heated thermal probe was placed on the scapular area of the subject 30 minutes after treatment with the test product or with the corresponding placebo. The value of the temperature considered painful by the subject was measured. 0.5 ml of an emulsion prepared according to Example VII, containing 0.5% of an extract of Zanthoxylum bungeanum prepared according to Example I, was administered. The results reported in the following table show the analgesic activity of the tested extract.

TABLE 1

Analgesic activity of tested extract versus placebo

| Treatment | $T_0$ | $T_{30\ min}$ |
|---|---|---|
| Placebo | 45.7 ± 1.0 | 45.3 + 0.4 |
| Extract | 46.0 + 0.8 | 47.2 + 0.4 |

The extracts of the invention can be formulated as creams, lotions, foams, or gels for administration to the skin or mucosas, or as soft-gelatin capsules, hard-gelatin capsules, tablets or suppositories. Preferably the extract of the invention is formulated in creams or foams for cutaneous treatment or in soft-gelatin capsules, chewable tablets or suppositories for the systemic route.

The extract dosages in the formulations range between 5 and 100 mg per dose in the formulations for the systemic use, whereas they vary from 0.05 to 1% in the topical formulations.

EXAMPLES

The following examples further illustrate the invention without limiting it.

EXAMPLE I—Preparation of a *Zanthoxylum bungeanum* Lipophilic Extract

10 Kg of pericarp of *Zanthoxylum bungeanum* are extracted according to the procedure reported below in a 25 L extraction plant for supercritical gas, equipped with two separators as condensers for fractioning the extract.

10 Kg of pericarp mechanically dried after harvesting at a temperature not higher than 60° C. was extruded into cubes and extracted with $CO_2$ in supercritical conditions under the following experimental conditions:

temperature: 35° C. in the extractor, 30° C. in the first separator and 20° C. in the second separator;

pressure: 180 bars in the extractor, 100 bars in the first separator and 50 bars in the second separator.

The $CO_2$ flow was 10 L per minute for 45 minutes. The extract was concentrated in the second separator, whereas most water present in the vegetable matrix was concentrated in the first separator. After drying the extract in the second separator under vacuum at a temperature not above 40° C., 1.5 Kg of pasty extract was obtained, which was slightly colored yellow, intensely scented, and had a isobutylamide content of about 25% by weight. HPLC analysis was carried out on a Hibar RT LiChrospher 100RP-18 column with the elution profile (1 mL/min) reported in Table 2. The injected amount was 5 mL of a 2 mg/mL solution. The chromatogram is reported in FIG. 1.

TABLE 2

HPLC analysis results for Example I

| TIME (min.) | WATER (%) | ACETONITRILE (%) | NUMBER OF THE GRADIENT CURVE |
|---|---|---|---|
| 0 | 60 | 40 | — |
| 20 | 60 | 40 | 6 |
| 30 | 10 | 90 | 6 |
| 35 | 60 | 40 | 6 |
| 40 | 60 | 40 | 6 |

EXAMPLE II—Preparation of a *Zanthoxylum bungeanum* Lipophilic Extract

10 Kg of pericarp mechanically dried after harvesting at a temperature not higher than 60° C. was extruded into cubes and extracted with $CO_2$ in supercritical conditions under the following experimental conditions:

temperature: 40° C. in the extractor, 30° C. in the first separator and 20° C. in the second separator;

pressure: 205 bars in the extractor, 100 bars in the first separator and 50 bars in the second separator. The $CO_2$ flow was 10 L per minute for 45 minutes. The extract was concentrated in the second separator, whereas most water present in the vegetable matrix was concentrated in the first separator. After drying the extract in the second separator under vacuum at a temperature not above 40° C., 1.5 Kg of pasty extract was obtained, which was slightly colored yellow/green and had the same chemical-physical characteristics as the extract of example I, and about a 20% isobutylamide content.

EXAMPLE III—Preparation of a *Zanthoxylum bungeanum* Lipophilic Extract

10 Kg of pericarp mechanically dried after harvesting at a temperature not higher than 60° C. was extruded into cubes and extracted with $CO_2$ in supercritical conditions under the following experimental conditions: temperature in the extractor 40° C. and pressure 230 bars. The ratio of $CO_2$ used for the extraction of the drug to be extracted was 27–45 Kg per Kg of drug. The extract was concentrated in a separator under 50 bars at 20° C. After drying under vacuum at a temperature not higher than 40° C., 1.3 Kg of pasty extract was obtained, which was slightly colored yellow/green, and had the same chemical-physical characteristics as the extract of Example I.

EXAMPLE IV—Preparation of a Purified Lipophilic Extract of *Zanthoxylum bungeanum*

0.5 Kg of lipophilic extract of pericarp of *Zanthoxylum bungeanum* prepared according to Example I was dissolved in 2.5 L of 95% aqueous methanol and extracted three times with 0.5 L each of n-hexane. The hexane phase was counter-washed with methanol using as marker the isobutylamides which should remain in the methanol phase. The inactive hexane phase was removed, whereas the methanol ones were combined, diluted with 0.6 L of water and re-extracted twice with 0.6 L of n-hexane. The combined hexane phases were decolorized with 0.3% charcoal, dried over $Na_2SO_4$ and concentrated to an oil at a temperature not higher than 40° C. under vacuum to obtain 0.22 Kg of an oily extract with honey-like consistence, having an isobutylamide content of about 50%.

EXAMPLE V - *Zanthoxylum bungeanum* alcoholic solution 100 ml contains:
| | |
|---|---|
| Zanthoxylum Bungeanum 20% solution in Oleyl Alcohol | 0.50 g |
| Cyclomethicone | 20.00 g |
| Alcohol | 100.0 ml |

EXAMPLE VI- *Zanthoxylum bungeanum* analcoholic solution 100 ml contains:
| | |
|---|---|
| Zanthoxylum Bungeanum 20% solution in Oleyl Alcohol | 0.50 g |
| PPG-26 Buteth 26 and PEG-40 Hydrogenated Castor Oil | 5.00 g |
| Methyl Chloroisothiazolinone and Methyl Isothiazolinone | 0.10 g |
| Purified water q.s. to | 100.0 ml |

EXAMPLE VII - *Zanthoxylum bungeanum* emulsion 100 g contains:
| | |
|---|---|
| Zanthoxylum Bungeanum 20% solution in Oleyl Alcohol | 0.50 g |
| Isohexadecane | 5.00 g |

-continued

| | |
|---|---|
| Glycerin | 4.00 g |
| $C_{12-15}$ Alkyl Benzoate | 2.00 g |
| Cyclomethicone | 2.00 g |
| PEG-20 Glyceryl Stearate and Lanolin wax | 1.00 g |
| Acrylates/$C_{10-30}$ Alkyl Acrylate Crosspolymer | 0.50 g |
| Cetyl Alcohol | 0.50 g |
| Imidazolidinyl urea | 0.30 g |
| Phenoxyethanol | 0.50 g |
| Methyl paraben | 0.20 g |
| Tocopherol | 0.10 g |
| Disodium EDTA | 0.10 g |
| Water q.s. to | 100.0 g |

EXAMPLE VIII- *Zanthoxylum bungeanum* fluid emulsion 100 g contains:

| | |
|---|---|
| *Zanthoxylum Bungeanum* 20% solution in Oleyl Alcohol | 0.50 g |
| PEG-20 Glyceryl Stearate and Glyceryl Stearate | 10.00 g |
| $C_{10-18}$ Triglycerides | 10.00 g |
| Glycerin | 5.00 g |
| Wheat Germ Oil | 2.00 g |
| Dimethicone | 2.00 g |
| PPG-25 Laureth-25 | 2.00 g |
| Cetyl Alcohol | 1.00 g |
| Hydroxylated Lanolin | 0.50 g |
| Imidazolidinyl urea | 0.30 g |
| Hectorite (e) Hydroxyethyl | 0.50 g |
| Phenoxyethanol and Methylparaben and Ethylparaben and Propylparaben and Butylparaben | 0.50 g |
| Tocopherol | 0.10 g |
| Water q.s. to | 100.0 g |

While the invention has been illustratively described herein with reference to specific aspects, features and embodiments, it will be appreciated that the utility and scope of the invention is not thus limited and that the invention may readily embrace other and differing variations, modifications and other embodiments. The invention therefore is intended to be broadly interpreted and construed, as comprehending all such variations, modifications and alternative embodiments, within the spirit and scope of the ensuing claims.

What is claimed is:

1. An extract of *Zanthoxylum bungeanum* having analgesic activity, obtained by extracting the pericarp of *Zanthoxylum bungeanum* with supercritical $CO_2$.

2. The extract according to claim 1 having an isobutylamide content from 20 to 50% by weight.

3. A pharmaceutical composition in the form of a cream, lotion, foam, gel, capsule, tablet or suppository and containing, as an active ingredient, the extract of claim 1 in an amount sufficient to provide analgesic activity.

4. A cosmetic composition in the form of a cream, lotion, foam, or gel and containing, as an active ingredient, the extract of claim 1 in an amount sufficient to provide analgesic activity.

5. The extract of claim 1, wherein the extracting with supercritical $CO_2$ is conducted at a temperature of between 35 and 55° C. and a pressure of between 250 and 300 bars.

6. The extract of claim 5, wherein the extracting with supercritical $CO_2$ is conducted at a temperature between 35 and 40° C. and a pressure of between 180 and 230 bars.

* * * * *

UNITED STATES PATENT AND TRADEMARK OFFICE
CERTIFICATE OF CORRECTION

PATENT NO. : 6,419,950 B2
DATED : July 16, 2002
INVENTOR(S) : Ezio Bombardelli et al.

It is certified that error appears in the above-identified patent and that said Letters Patent is hereby corrected as shown below:

Column 6,
Line 24, replace "250" with -- 150 --.

Signed and Sealed this

Fifth Day of November, 2002

Attest:

Attesting Officer

JAMES E. ROGAN
Director of the United States Patent and Trademark Office